United States Patent [19]

Trinel et al.

[11] 4,116,631

[45] Sep. 26, 1978

[54] METHOD FOR MICROBIOLOGICAL ANALYSIS OF LIQUID MEDIUMS

[76] Inventors: Pierre-Andre Trinel; Henri Leclerc, both c/o Inserm Unite 146 Certia 369, rue Jules-Guesde, 59650 Villeneuve-d'Ascq; Yves Moschetto, c/o Centre de Technologie Biomedicale Inserm, 13 rue Camille Guerin, 59000 Lille, all of France

[21] Appl. No.: 767,314

[22] Filed: Feb. 10, 1977

[30] Foreign Application Priority Data

Feb. 19, 1976 [FR] France .................................. 76 05166

[51] Int. Cl.² .................... G01N 1/18; G01N 21/26; G01N 33/16
[52] U.S. Cl. ............................. 23/230 B; 23/230 R; 195/103.5 R
[58] Field of Search ............. 23/253 R, 230 R, 230 B; 195/103.5 R

[56] References Cited

U.S. PATENT DOCUMENTS 3,479,141  11/1969  Smythe et al. ...................... 23/253 R

OTHER PUBLICATIONS

Ferrari et al, "A Completely Automated System for the Chemical Determination of Streptomycin and Penicillin in Fermentation Media", Anal. Chem., 1959, 31, 1710–1717.

*Primary Examiner*—R.E. Serwin
*Attorney, Agent, or Firm*—Robert E. Burns; Emmanuel J. Lobato; Bruce L. Adams

[57] ABSTRACT

A method of transporting liquid samples of bacteria cultures for microbiological analysis in an automatic analysis apparatus. The culture samples are transported in a liquid stream in a conduit as samples separated by intermediate segments of a decontamination solution effective to decontaminate the conduit of bacteria in the next preceeding sample to insure freedom of decontamination from one sample to the other. The spacing of the samples includes spacing the sample from the decontamination solution with segments of an inert gas.

4 Claims, 2 Drawing Figures

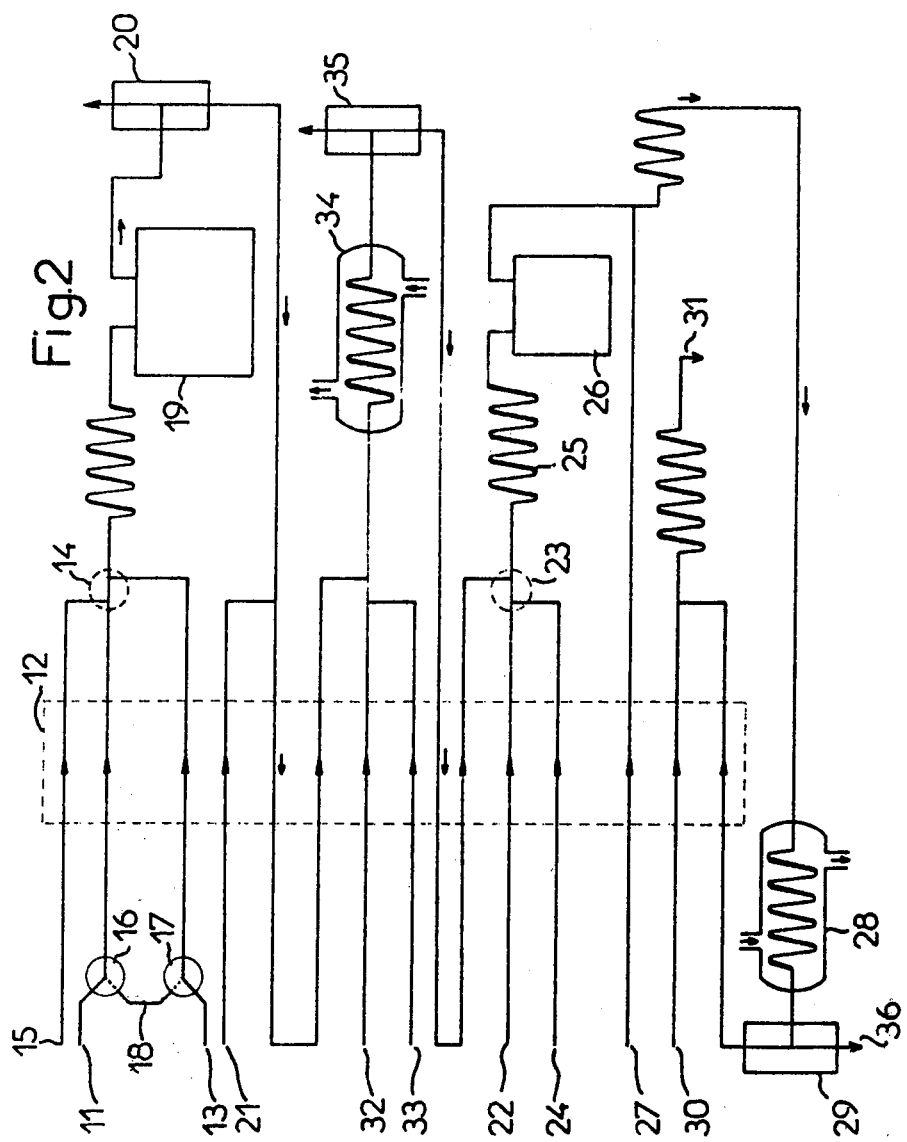

METHOD FOR MICROBIOLOGICAL ANALYSIS OF LIQUID MEDIUMS

BACKGROUND OF THE INVENTION

The present invention relates to a bacteriological investigation method particularly intended for the microbiological analysis of liquid mediums.

This method may be applied generally to the identification of one or more bacteria in a liquid medium. The following bacterial species may be mentioned by way of example: Escherichia coli, Klebsiella, Citrobacter, Enterobacter, Aeromonas, Pseudomonas aeruginosa, Staphylococcus, Streptococcus and Bacillus.

The method has been used by the inventors, in the premises of the Pasteur Institute in LILLE, for the bacteriological testing of water.

The bacteriological investigation method developed by Pasteur more than a century ago is presently in current use, since its exactness and efficiency are well established.

However, the applications of this method are limited: in fact, it always makes use of solely manual techniques and the times required for analysis are considerable. Microbiological analyses firstly require the making of selective or non-selective cultures of the germs to be identified, then a stage for the isolation of the various bacterial species present, since identification generally proceeds from a "pure culture". The identification of bacterial species is therefore possible; it requires a frequently high number of biochemical tests.

This well known method always uses manual techniques requiring the intervention of a technician at all stages. It is divided into several stages and uses a large number of culture mediums for isolating and identifying a bacterial species. The response times are of the order of 24 hours to 3 days depending on whether the test is negative or positive.

It has therefore become indispensable to develop a method of bacteriological investigation using an automated method whose response time would be reduced considerably and whose cost price would be much lower.

If it has seemed necessary to automate biological investigation, it has also become indispensable to develop a method which may be carried out continuously. In fact, it is quite useless to improve the sensitivity of known manual methods for samples which are in no way representative. This is particularly the case when one analyses a sample of several milliliters of water taken from a river or pipe which frequently contains several thousands of cubic meters.

The main idea of the method according to the invention has been to link the taking of samples and the analysis to make the method completely automatic and to enable it to be carried out continuously.

Continuous automatic analysers are currently known, which are used for example in the chemical field or in the analysis of blood, which analysers suck in the samples from a pipe through the intermediary of a pump, whilst dividing the latter into segments by means of a gas or liquid. It has not been possible for these apparatus to be applied directly to microbiological analysis and the inventors have come up against the main drawback inherent in the type of sample used and even in the apparatus, namely that of rinsing. In fact, the problem of the separation of samples, common to all chemical analyses and conditioning the speed of sampling has become more precisely in this case, a problem of decontamination made more complex by two main reasons:

— firstly, the unusual length of the circuit and the time taken by the samples to pass through this circuit have nothing in common with those of chemical circuits and favour greater progressive contamination.

— then, the circuit envisaged in this case is a living circuit which may thus be subject to perpetual evolution: in chemical circuits, a molecule or atom passing from one sample to another, remains as it is in the contaminated sample; on the contrary, in a bacteriological circuit, if a bacterium passes from one sample to the next, it multiplies rapidly in the latter.

SUMMARY OF THE INVENTION

To remedy these drawbacks and propose a method for continuous bacteriological investigation, it has therefore become necessary to find a decontamination solution which can be used during the investigation of all bacterial species. To this end, the method according to the invention is characterised by the fact that it consists of taking the liquid to be analysed from a pipe, of dividing the portion withdrawn into samples by separating them with a decontamination solution which is active with regard to the bacteria being investigated, of moving the arrangement in the pipe by forced circulation and of subjecting the samples to the various stages necessary for the analysis.

This continuous method has the advantage of being able to be applied to all bacterial species and its automation will be described hereafter in the case of the bacteriological testing of water.

BRIEF DESCRIPTION OF THE DRAWINGS

FIG. 2 is a diagram of an installation facilitating continuous automatic testing of the water.

DESCRIPTION OF THE PREFERRED EMBODIMENTS

Figure 1:
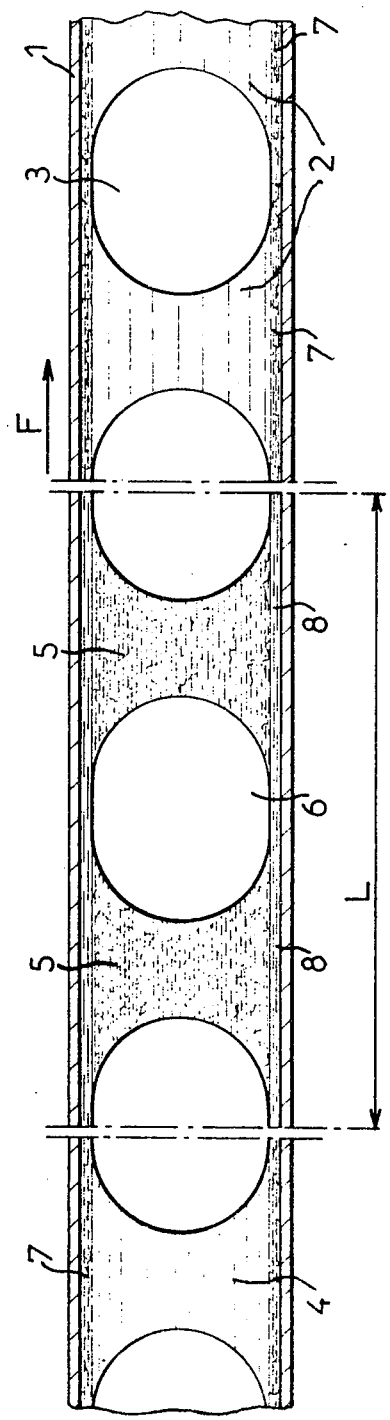
FIG. 1 is a partial view of a pipe of the apparatus used.

In order to be able to use commercially available automatic analysers with continuous flow, a decontamination solution has been sought, which is capable of causing considerable slowing down of the growth of bacteria brought into contact with the latter or better still, having a bactericidal power. This solution should also have no bacteriostatic action, when it diffuses partially in the samples. To obtain optimum decontamination of the circuits of an apparatus with continuous flow, it was necessary that the decontamination time of the solution was of the order of a minute.

For carrying out the method, analysis of the various samples is carried out automatically using an automatic analyser of the "TECHNICON" type. This type of apparatus and its principle are currently known to a man skilled in the art and for any details on this subject, reference should be made in particular to the works of:

(1) M. CAMIER and P. GONNARD.

In automat. anal. chem. Technicon symp. II. Paris, 1966. Dosage automatique de décarboxylase d'acides amines (Automatic analysis of amino acid decarboxylase)

(2) A. FERRARI, F. M. RUSSO ALESI and J. M. KELLY

A completely automated system for the chemical determination of streptomycin and penicillin in fermentation media Anal. chem., 1959, 31, 1710

(3) S. POSEN; D. H. BIRKETT, A. J. CONYERS, C. H. CORNFISH and F. C. NEALE.

In "automat. anal. chem." Technicon Symp. NEW YORK 1967 Automated methods in the study of enzyme kinetics.

In order to illustrate the necessary properties of the decontaminating solution, FIG. 1 is a partial view of a pipe or conduit carrying the continuous flow. A sample 2 to be analysed and divided by a multitude of microbubbles of air 3 is taken from this pipe 1. In the pipe 1, the sample occupies a length of 40 to 80 cm. Two consecutive samples 2 and 4 are separated by a distance L occupied by the decontamination solution 5, itself separated by micro-bubbles of air 6. The system of liquids and micro-bubbles moves by forced circulation in the direction of arrow F for example.

In FIG. 1, the quantity of liquid deposited on the walls of the pipe 1 has been exaggerated, for the sake of a better understanding. A small quantity of decontaminating solution, which has preceded the sample 2, is located at 7, i.e. in contact with the sample 2. A small quantity of liquid coming from the sample 2 is located at 8, i.e. in contact with the decontaminating solution.

FIG. 1 illustrates the two main properties which the decontaminating solution must have:

(1) the walls of the sections of pipe contaminated at 8 by the passage of the preceding sample 2 must be decontaminated by the bactericidal action of the decontamination solution 5 in order to prevent the addition and development of bacteria foreign to the following sample. This decontamination should be obtained after a contact of the order of 1 minute to facilitate continuous rapid analysis. The length L of decontaminating solution in the pipe will be chosen in relation to its bactericidal power and the rate of flow in order to obtain a contact time of the order of 1 minute.

(2) The decontamination solution 7 which is located in a small quantity in the region of the walls of the sections of pipe containing the sample 2 or 4 should have no bactericidal action in the case where it diffuses in the following samples so as not to falsify the analysis.

To verify the first property, we have thus shown the bactericidal power of certain decontaminating solutions before checking that this bactericidal power was real with regard to all the bacteria.

Test 1

One verified the bactericidal power of the following buffer solutions used at the concentrations shown:
Buffer 1 : 0.2M KCl — HCl buffer pH 1.9
Buffer 2 : 0.1M glycocolle — HCl buffer pH 2.4
Buffer 3 : 0.1M citrate — $PO_4 HNa_2$ buffer pH 2.5
Buffer 4 : 0.1M acetate buffer pH 3.3
Buffer 5 : 0.07M phthalate buffer pH 2.4
Buffer 6 : 0.03M benzoate buffer pH 3
Buffer 7 : 0.03M salicylate buffer pH For this study, 1 ml of a recent culture of Escherichia coli is added to 9 ml of the various buffers 1 to 7. After 1 minute and 1 hour of contact, 1 ml of the various suspensions is removed and placed in a culture with stirring at 37° C. in 50 ml selective bouillon. The growth is followed as regards optical density at 640 mμ (Jouan Junior Spectrophotometer).

It is found that a residence time of 1 minute in the KCl — HCl buffer does not retard the growth. This slowing down is negligible for buffers 2 to 4. Even a residence time of 1 hour in the various buffers 1 to 4 causes only slight slowing down of the growth.

The buffers 5, 6, 7 have a bactericidal action on Escherichia coli after 1 minute. Although the inoculum is considerable, the test shows that no bacteria can live after a residence time of 1 minute.

The phthalate/HCl decontamination solution used in the preceding example was prepared in the following manner: 500 ml of a 0.07 M solution of potassium phthalate were added to 396 ml 0.07 M hydrochloric acid. The pH is 2.4.

Test 2

The bactericidal power of this solution is linked with the pH, as shown in the following test:

Decontaminating solutions of the same concentration were prepared with a different pH value (solution I at pH 3; solution II at pH 4; solution III at pH 5), 1 ml of a recent culture of Escherichia coli is mixed with 9 ml of each of the solutions I, II and III as well as with 9 ml distilled water (control). After 1 minute of contact, 1 ml of the various mixtures is removed and incubated in 50 ml culture medium. The development of the optical density in the various flasks shows that the growth of the cultures differs depending on the conditions to which they are subjected: 1 minute of contact with the solution at pH 5 causes only slight slowing down of the growth, whereas 1 minute of contact with the solution at pH 3 prevents any subsequent growth of bacteria as previously.

Test 3

The decontaminating solution chosen may be used during any continuous method of microbiological analysis owing to the fact that its bactericidal action is real on bacterial strains other than Escherichia coli. To reveal this, one proceeded as previously, mixing 1 ml of a recent culture of the bacterial species tested with 9 ml of the decontaminating solution I. After 1 minute of contact, 1 ml of the various mixtures was removed and incubated in 50 ml culture medium. The controls are always obtained by incubating 1 ml of a tenfold dilution of these same cultures in 50 ml of the medium.

| CULTURE AFTER 24 HOURS INCUBATION at 37° C | | |
|---|---|---|
| Operating conditions before making the culture species studied | Control | 1 minute in the decontaminating solution |
| E. coli | + | − |
| Klebsiella | + | − |
| Citrobacter | + | − |
| Enterobacter | + | − |
| Aeromonas | + | − |
| Pseudomonas aeruginosa | + | − |
| Staphylococcus | + | − |
| Streptococcus | + | − |
| Bacillus | + | − |

The above table shows that for all the bacterial species tested, a residence time of 1 minute in the decontaminating solution having a pH of 3 was sufficient to completely inhibit their culture.

To verify the second property which the decontaminating solution should have, i.e. the absence of bactericidal action at the time of partial diffusion of this solution in the culture medium, the following test was carried out:

Simultaneous cultures of Escherichia coli were produced at 40° C. in flasks containing 80 ml culture medium and having increasing concentrations of the 0.07 M phthalate decontaminating solution, pH 2.4:

| Flask I   | : | control without decontaminating solution, |
|-----------|---|--------------------------------------------|
| Flask II  | : | final concentration of decontaminating solution $= \frac{1}{9}$ of the bactericidal concentration of the decontaminating solution, |
| Flask III | : | final concentration of decontaminating solution $= \frac{2}{9}$ of the bactericidal concentration of the decontaminating solution, |
| Flask IV  | : | final concentration of decontaminating solution $= \frac{3}{9}$ of the bactericidal concentration of the decontaminating solution, |
| Flask V   | : | final concentraion of decontaminating solution $= \frac{4}{9}$ of the bactericidal concentration of the decontaminating solution. |

If one compares with the spectrophotometer the development of the cultures in the various flasks, one will see that the growth of the Escherichia coli in flasks II to IV is slowed down very little or not at all by the various concentrations of decontaminating solution which they contain. However, in flask V, where the concentration of decontaminating solution approaches half the bactericidal concentration used previously, the growth is as rapid as in the control flask. One notes solely a slightly lower optical density when the stationary phase is reached. This is a consequence of the partial acidification of the culture medium favouring the bactericidal action of the decontamination solution.

It is doubtful whether the diffusion of the decontamination solution in the culture medium at the time of the culture in the pipe of the apparatus allows a concentration similar to that of flask V, this is why the buffer decontamination solutions chosen from phthalate, benzoate or salicylate have given excellent results when they have been used for the continuous bacteriological testing of water.

It has been shown that the decontamination solution had a bactericidal power with an acid pH and that this power was completely cancelled out when the pH approached neutrality, comprised between 6 and 8, at which one generally grows cultures. The partial diffusion of the decontaminating solution thus has no effect on the following samples.

The method according to the invention has been successfully applied to the continuous bacteriological testing of water by the investigation of Escherichia coli. The decontamination solution in question enabled the inventors to use a conventional continuous flow automatic analyser by adapting it to the investigation of Escherichia coli by measuring the activity of glutamic acid decarboxylase. To carry out accurate measurement of Escherichia coli, one thus investigated the optimum conditions for revealing the enzyme in order that the measurement is undertaken when the enzyme has achieved an optimum activity on the proliferating cultures.

Measurement of the enzyme will be carried out on the basis of the following reaction:

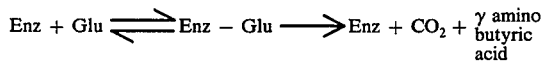

The $CO_2$ liberated by the reaction of the enzyme on glutamic acid will then be measured under optimum operating conditions, which will be defined hereafter.

Four parameters influencing the optimum conditions for revealing the enzyme have been studied:

(1) The kinetics of the reaction have been studied in order to provide an optimum length of the coil of the automatic analyser before carrying out the measurement of the $CO_2$. It was noted that the speed of the reaction was maximum for approximately 8 minutes, then decreased gradually and disappeared after 25 minutes. In the part of the apparatus preceding the measurement of the $CO_2$, it will therefore be necessary to provide a length of coil sufficient to allow a reaction time of 30 minutes and thus to undertake the measurement with optimum sensitivity.

(2) The effect of the temperature was studied by measuring at different temperatures of between 30° and 55° C., the kinetics of the reaction of the same bacterial suspension under the same operating conditions. Comparison of the curves of the various kinetics indicates optimum activity of the enzyme at 45° C.

(3) Study of the influence of the pH gives an optimum activity at a pH of 3.8 for the glutamic acid decarboxylase. A reduction of the pH rapidly causes complete deactivation of the enzyme at pH 3.

(4) The effect of the concentration of glutamic acid, occurring in the enzymatic reaction, has also been studied. For a reaction time of 30 minutes, it was shown that the concentration of glutamic acid should be from 1.5 to 1.8 grams per 100 ml, in order to facilitate optimum enzymatic reaction and therefore better measurement.

The optimum conditions for the formation of glutamic acid decarboxylase in the culture medium have also been studied:

(1) Measurements of the activity of the enzyme undertaken during the stage of growth and at the end of the growth have not made it possible to establish any significant difference, whether the cultures are incubated in the presence or absence of glutamic acid. Therefore, it has not seemed necessary to induce the decarboxylase.

(2) The influence of the culture phase was followed by measurement of the enzymatic activity during growth. The results indicate that the decarboxylase is not synthesized from the beginning of the growth, but that it is only produced in the last third of the exponential phase of growth, its rate thus increasing very rapidly to reach its maximum within several hours. The formation of decarboxylase stabilises after a time of the order of 4 hours, but if incubation of the culture is continued beyond 24 hours, the activity increases slightly.

(3) The effect of the culture temperature was tested between 30° and 44° C. The optimum formation of the enzyme is located between 37° and 42° C. The synthesis is most active at 40° and 42° C.

(4) In order to discover the pH most favourable to the formation of decarboxylase, culture mediums buffered with phosphates were tested at pH values of between 5.5 and 7.8. Measurement of the activity and of the various cultures carried out on the same suspensions reveals an optimum formation of decarboxylase in a slightly acid medium. The most favourable pH is 6.8.

Since the optimum conditions for the formation of the enzyme in the cultures as well as the optimum conditions for revealing the enzyme have been defined, the installation facilitating an automatic and continuous bacteriological control of the water by Escherichia coli will be described hereafter with reference to FIG. 2.

The sample of water is drawn in at 1 by a pump shown diagrammatically at 2. It is mixed with a culture medium drawn in at 3, the system being divided into segments at 4 by microbubbles of air from which the $CO_2$ has been removed, which are admitted at 5. The valves 16 and 17 are in the position illustrated in FIG. 2, during the period of formation of the sample over the length L of FIG. 1. When this length is reached, the valves are turned into the position shown in broken line in FIG. 2 to facilitate the admission of the decontamination solution at 18. The latter is also divided into segments at 14 by micro-bubbles of air. A succession of segments of the sample and decontaminating solution move by forced circulation towards incubation coils located in a vessel 19 kept in a water bath at 41° C. They move in this vessel for several hours and it is during this incubation that the decarboxylase is synthesized.

The cultures then pass through a bubble removing device 20 which eliminates the air dividing the liquid flow into segments, as well as the very abundant fermentation gases. After having been diluted by one third for example with the water admitted at 21, the liquid flux is then measured according to optimum conditions for revealing the enzyme, already described.

The culture samples leaving 20 are at a temperature of 41° C. and have a pH 6. Under these conditions, some dissolved $CO_2$ remains in the liquid, which should be eliminated before carrying out the measurement, in order to prevent interference with the decarboxylation $CO_2$.

This elimination takes place by increasing the temperature and lowering the pH, for example by means of a 0.1 M buffer solution of sodium acetate, pH 3.4 injected at 32. This buffer solution is only added to the segments constituting the samples, the segments of decontaminating solution continuing their rinsing function in the circuit. The samples are once more separated by micro-bubbles of air admitted at 33. The increase in temperature is produced in the exchanger 34 and the $CO_2$ from breathing which is undesirable, is eliminated at the bubble-removing device 35.

A mixture of glutamic acid at a rate of 15 grams per liter and a 0.1M acetate buffer having a pH of 3.9 is admitted at 22 for this purpose, which will be mixed with the samples, then divided into segments at 23 by the air from which $CO_2$ has been removed and which is admitted at 24. The samples and the decontaminating solution will circulate in the vessel 26 kept at 45°, for 30 minutes and it is during this stage that the glutamic acid will be transformed into γ amino butyric acid and $CO_2$ which remains in solution in the medium. Since the optimum conditions for revealing the enzyme have been provided, the $CO_2$ is then liberated in gaseous form in the following stage, by the joint action of acidification and an increase in temperature. The acidification is obtained by normal sulphuric acid admitted at 27, whereas the temperature of the sample is raised to 50° by means of the exchanger 28. The bubbles of air which divide the liquid flux into segments are regularly enriched with $CO_2$ owing to the liberation of gas in the gaseous form. The gaseous mixture is recovered proportionally by means of a $CO_2$ trap 29. The air and the $CO_2$ may thus come into contact with a phenol phthalein reagent stabilized by a carbonate buffer admitted at 30. Decoloration of the reagent which depends on the concentration of $CO_2$ is measured at 31 by a colorimeter ($\lambda = 550$ nm) and a recorder inscribes the variation in the form of a peak.

The decontaminating solution and samples are discharged at 36.

The analyser which has been described is entirely automatic and it has the advantage of coupling continuous sampling with continuous analysis.

We claim:

1. A method of transporting liquid samples for microbiological analysis in an automatic analysis apparatus comprising, spacing apart in a fluid stream in a conduit successive liquid biological samples by intermediate segments of a decontamination solution effective to decontaminate the conduit of bacteria in the next preceeding sample to insure freedom of contamination from one sample to the other, said spacing including spacing the liquid biological samples and intermediate decontamination solution with inert gas segments, transporting the stream through said conduit, and said segments of decontamination solution having a length effective to allow said solution to decontaminate the conduit in dependence upon the rate of flow of said stream.

2. A method of transporting liquid samples for microbiological analysis in an automatic analysis apparatus according to claim 1, in which said decontamination solution comprises a salt selected from the group of a salt of phthalic, benzoic or salicylic acids.

3. A method of transporting liquid samples for microbiological analysis in automatic analysis apparatus according to claim 1, in which said liquid samples each comprise a bacteria culture having a pH between 6 and 8 and wherein said decontamination solution has a pH between 2 and 5.

4. A method of transporting liquid samples for microbiological analysis in an automatic analysis apparatus according to claim 1, in which said decontamination solution is a buffer solution.

* * * * *